US008377671B2

(12) United States Patent
Cournac et al.

(10) Patent No.: US 8,377,671 B2
(45) Date of Patent: Feb. 19, 2013

(54) [NIFE]-HYDROGENASES HAVING AN IMPROVED RESISTANCE TO DIOXYGEN, PROCESS FOR OBTAINING THEM AND THEIR APPLICATIONS

(75) Inventors: Laurent Cournac, La Tour d'Aigues (FR); Anne Volbeda, Le Touvet (FR); Marc Rousset, Gemenos (FR); Emeline Aubert-Jousset, Bouc Bel Air (FR); Geneviève Guedeney, Manosque (FR); Sébastien Dementin, Ballan-Mire (FR); Christophe Leger, Marseilles (FR); Fanny Leroux, Genicourt (FR); Stéphanie Champ, Marseilles (FR)

(73) Assignee: Commissariat a l'Energie Atomique, Paris (FR)

( * ) Notice: Subject to any disclaimer, the term of this patent is extended or adjusted under 35 U.S.C. 154(b) by 226 days.

(21) Appl. No.: 12/671,555

(22) PCT Filed: Aug. 1, 2008

(86) PCT No.: PCT/IB2008/002998
§ 371 (c)(1),
(2), (4) Date: Jun. 1, 2010

(87) PCT Pub. No.: WO2009/019613
PCT Pub. Date: Feb. 12, 2009

(65) Prior Publication Data
US 2011/0212502 A1    Sep. 1, 2011

(30) Foreign Application Priority Data

Aug. 3, 2007   (EP) .................................... 07290973

(51) Int. Cl.
*C12N 9/02*     (2006.01)
*C12N 1/20*     (2006.01)
*C12P 21/06*    (2006.01)
*C12P 19/34*    (2006.01)
*C07H 21/04*    (2006.01)
*C07H 21/00*    (2006.01)
*C07K 1/00*     (2006.01)

(52) U.S. Cl. ..................... 435/189; 435/69.1; 435/252.3; 435/320.1; 435/91.1; 536/23.1; 536/23.2; 536/25.3; 530/350

(58) Field of Classification Search .................. 435/189, 435/69.1, 252.3, 320.1, 91.1; 536/23.1, 23.2, 536/25.3; 530/350
See application file for complete search history.

(56) References Cited

FOREIGN PATENT DOCUMENTS
WO    WO 2004/093524 A2    11/2004

OTHER PUBLICATIONS

Broun et al., Catalytic plasticity of fatty acid modification enzymes underlying chemical diversity of plant lipids. Science, 1998, vol. 282: 1315-1317.*

Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Duche et al., Enlarging the gas access channel to the active site renders the regulatory hydrogenase HupUV . . . FEBS Journal., 2005, vol. 272: 3899-3908.*
Kisselev L., Polypeptide release factors in prokaryotes and eukaryotes: same function, different structure. Structure, 2002, vol. 10: 8-9.*
Vignais et al., Classification and phylogeny of hydrogenases. FEMS Microbiol. Rev., 2001, vol. 25: 455-501.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Buhrke, T. et al., *Oxygen Tolerance of the $H_2$-sensing [NiFe] Hydrogenase from Ralstonia Eutropha H16 Is Based on Limited Access of Oxygen to the Active Site*, The Bournal of Biological Chemistry, vol. 280, No. 25, Jun. 2005, pp. 23791-23796.
De Lacey, A. L. et al., *Native and Mutant Nickel-Iron Hydrogenases: Unravelling Structure and Function*, Coordination Chemistry Reviews, 249, (2005), pp. 1596-1608.
Fontecilla-Camps, J. C. et al., *Hydrogen Biocatalysis: A Tale of Two Metals*, TIBTECH, vol. 14, Nov. 1996, pp. 417-420.

(Continued)

*Primary Examiner* — Ganapathirama Raghu
(74) *Attorney, Agent, or Firm* — Alston & Bird LLP

(57) ABSTRACT

The invention relates to [NiFe]-hydrogenases having an improved resistance to dioxygen, said [NiFe]-hydrogenases may be obtained by:—providing an initial polynucleotide comprising a sequence encoding a large subunit of a [NiFe]-hydrogenase, said large subunit comprising the following peptide motifs: •L1: RGXE, wherein X=L, I, F, V or M•L2: [R/K]$X_1$C[G/R]$X_2$C, wherein Xi is any amino acid residue, $X_2$=L, V, I or M; L1 and L2 being separated by 16 any amino acid residues; •L3: $X_1X_2X_3X_4X_5X_6X_7X_8X_9X_{10}X_{11}X_{12}$[D/S/E], wherein $X_1$=D, S, N or E, $X_2$=H, D, S, N or L, $X_5$=H, S, A, Q or W, $X_6$=F, T, Y or G, $X_9$=L, F, M or Y, the other $X_n$ being any amino acid residue; •L4: D[P/I/S]C$X_1X_2$C$X_3X_4$[H/R], wherein $X_2$=A, S, V, G or T, $X_1$, $X_3$ and $X_4$ are any amino acid residue • and optionally comprising a motif LO: R[I/V/A]EG[H/D/A].—modifying said initial polynucleotide in order to substitute at least one of the residues $X_2$ of motif L2 and Z or $X_4$ of motif L3 and Z or $X_9$ of motif L3 of said large subunit by a methionine.

27 Claims, 9 Drawing Sheets

OTHER PUBLICATIONS

Guiral, M. et al., *Hyperthermostable and Oxygen Resistant Hydrogenases From a Hyperthermophilic Bacterium Aquifex Aeolicus: Physicochemical Properties*, International Journal of Hydrogen Energy, 31, (2006), pp. 1424-1431.

Leroux, F. et al., *Experimental Approaches to Kinetics of Gas Diffusion in Hydrogenase*, PNAS, vol. 105, No. 32, Aug. 2008, pp. 11188-11193.

Matias, P. M. et al., *[NiFe] Hydrogenase From Desulfovibrio Desulfuricans ATCC 2774: Gene Sequencing, Three-Dimensional Structure Determination and Refinement at 1.8 Å and Modelling Studies of Its Interaction With the Tetrahaem Cytochrome $c_3$*, J. Biol. Inorg. Chem., 6, (2001), pp. 63-81.

Volbeda, A. et al., *High-Resolution Crystallographic Analysis of Desulfovibrio Fructosovorans [NiFe] Hydrogenase*, International Journal of Hydrogen Energy, 27, (2002), pp. 1449-1461.

Wawer, C. et al., *Genetic Diversity and Expression of the [NiFe] Hydrogenase Large-Subunit Gene of Desulfovibrio spp. in Environmental Samples*, Applied and Environmental Microbiology, vol. 63, No. 11, Nov. 1997, pp. 4360-4369.

International Search Report for Application No. PCT/IB2008/002998 mailed May 4, 2009.

\* cited by examiner

[NIFE]-HYDROGENASES HAVING AN IMPROVED RESISTANCE TO DIOXYGEN, PROCESS FOR OBTAINING THEM AND THEIR APPLICATIONS

CROSS REFERENCE TO RELATED APPLICATIONS

This application is a national stage application filed under 35 U.S.C. 371 of International Application No. PCT/IB2008/002998, filed Aug. 1, 2008, which claims priority from EP Application No. 07290973.2, filed Aug. 3, 2007.

FIELD AND BACKGROUND OF THE INVENTION

The invention relates to [NiFe]-hydrogenases having an improved resistance to dioxygen ($O_2$).

The use of hydrogen as a first energy vector is now widely recognized as a long-term solution from the point of view of clean and sustainable energy economy (CHORNET & CZERNIK, Nature, 418, 928-9, 2002).

Some photosynthetic organisms, belonging to the group of the green algae or cyanobacteria, possess hydrogenases, catalyzing the conversion between $H^+$ and $H_2$. The presence of hydrogenases confers to these organisms the ability to produce dihydrogen, starting from solar energy and using water as electron and proton donors. This type of biological conversion of light energy into hydrogen is one of the most efficient in terms of energy conservation, as 10% of the incident light energy can theoretically be recovered in hydrogen (PRINCE & KHESHGI, Crit. Rev. Microbiol., 31, 19-31, 2005). Due to their high catalytic turnover and their specificity towards $H_2$, hydrogenases are also envisioned as potential catalysts to replace platinum in fuel cells, through the design of so-called bio-fuel cells. Such a design might considerably alleviate the price of fuel cells in which both platinum and H+ selective membranes represent the major costs. It has also been proposed to use hydrogenases in designing biosensors, for safety applications (QIAN et al., Biosens Bioelectron, 17, 789-96, 2002; BIANCO, J Biotechnol, 82, 393-409, 2002). Thus, potential applications of hydrogenases include dihydrogen photoproduction, bio-fuel cells and biosensors.

Hydrogenases constitute a family of oxidoreductase enzymes which have been classified according to the metal content of their active sites (VIGNAIS et al., FEMS Microbiol Rev, 25, 455-501, 2001). The main classes are [NiFe]-hydrogenases and [FeFe]-hydrogenases, which are phylogenetically distinct families of proteins.

[NiFe]-hydrogenases have been isolated from diverse bacteria including for instance *Desulfovibrio, Azobacter, Rhodobacter, Ralstonia, Rhizobium, Bradyrhizobium*, and *Synechocystis*. These enzymes are also found in several archaea such as *Methanococcus, Methanosarcina, Acidianus, Pyrobaculum*. They typically comprise a large subunit, containing the Ni—Fe active site, and a small subunit containing [Fe—S] clusters involved in the electron transfer; they may also contain additional subunits. The large subunits of all [NiFe]-hydrogenases appear to be evolutionary related. They contain at least four conserved motifs, designated (from N-terminal to C-terminal) as L1, L2, L3, and L4. In certain archaea, the large subunit is truncated before L4, which motif is then contained in an additional very small subunit. A fifth conserved motif, designated as L0, is also found near the N-terminal end of most of [NiFe]-hydrogenases (KLEIHUES et al., J. Bacteriol., 182, 2716-24, 2000; BURGDORF et al., J. Bacteriol., 184, 6280-88, 2002).

These motifs are defined by the following consensus sequences (one-letter code):
L0: R[I/V/A]EG[H/D/A]
L1: RGXE, wherein X=L, I, F, V or M
L2: [R/K]$X_1$C[G/R]$X_2$C, wherein $X_1$ is any amino acid residue, $X_2$=L, V, I or M; L1 and L2 being separated by 16 any amino acid residues;
L3: $X_1X_2X_3X_4X_5X_6X_7X_8X_9X_{10}X_{11}X_{12}$[D/S/E], wherein $X_1$=D, S, N or E, $X_2$=H, D, S, N or L, $X_5$=H, S, A, Q or W, $X_6$=F, T, Y or G, $X_9$=L, F, M or Y, the other $X_n$ being any amino acid residue;
L4: D[P/I/S]C$X_1X_2$C$X_3X_4$[H/R], wherein $X_2$=A, S, V, G or T, $X_1$, $X_3$ and $X_4$ are any amino acid residue.

In said motifs, [aa1/aa2 . . . ] means that said amino acids are alternatives at a given position; any amino acid residue refers to a natural or synthetic amino acid including enantiomers and stereoisomers of any of the 20 usual amino acids; $X_n$ corresponds to all the other positions not specifically mentioned.

Each of motifs L2 and L4 contains two cysteine residues which are involved in the binding of nickel in the active site. Although L3 is rather variable, it is easily identified in a multiple sequence alignment by ClustalW [Chema R, Sugawara H, Koike T, Lopez R, Gibson T J, Higgins D G, Thompson J D (2003). Multiple sequence alignment with the Clustal series of programs. Nucleic Acids Res, 31:3497-3500]. The sequence of L3 is DHLVHFYHLHALD in *D. fructosovorans* [NiFe]-hydrogenase and SHALSFFHLSSPD in the *Synechocystis* PCC6803 enzyme.

Both [NiFe]-hydrogenases and [FeFe]-hydrogenases are $O_2$ sensitive. Generally, [Fe]-hydrogenases are irreversibly inactivated by $O_2$. In contrast, $O_2$-exposed [NiFe]-hydrogenases can be reactivated, and there are some examples of relatively oxygen-tolerant enzymes, such as MBH and SH from the Knallgas bacterium *Ralstonia eutropha* although they tend to be less active (BURGDORF et al., J Mol Microbiol Biotechnol, 10, 181-96, 2005). A sub-group of highly oxygen-tolerant but even less active [NiFe]-hydrogenases are the $H_2$-sensors such as RH from *Ralstonia eutropha* (BERNHARD et al., J Biol Chem, 276, 15592-7, 2001) and the HupUV proteins from *Rhodobacter capsulatus* (ELSEN et al., J Bacteriol, 178, 5174-81, 1996) and *Bradyrhizobium japonicum* (BLACK et al., J Bacteriol, 176, 7102-6, 1994), as well as [NiFeSc]-hydrogenases.

The sensitivity of hydrogenases to $O_2$ represents a major obstacle to the development of technological applications of these enzymes. For instance, because of hydrogenase inhibition by the dioxygen produced during water photolysis (LEGER et al., J Am Chem Soc, 126, 12162-72, 2004), photosynthetic production of dihydrogen is only a transient phenomenon under natural conditions (COURNAC et al., J Bacteriol, 186, 1737-46, 2004). As a result, actual dihydrogen production efficiencies obtained in laboratory experiments are lower than 1% (MELIS et al., Plant Physiol, 122, 127-36, 2000; FOUCHARD et al., Appl Environ Microbiol, 71, 6199-205, 2005).

Both [FeFe] hydrogenases and [NiFe]-hydrogenases possess hydrophobic gas channels allowing $H_2$ and also $O_2$ diffusion between the molecular surface and the active site. FIG. 1 represents the crystallographic structure of the prototypic [NiFe] hydrogenase from *D. fructosovorans*: the gas channels are shown in grey.

At the internal end of the hydrophobic channels, near the [NiFe] active site, two hydrophobic residues, usually a valine and a leucine that are conserved in oxygen-sensitive [NiFe]-hydrogenases, are respectively replaced by isoleucine and phenylalanine in the sub-class of oxygen-tolerant $H_2$-sensors (VOLBEDA et al., Int. J. Hydrogen Energy, 27, 1449-61, 2002). These correspond respectively to residue $X_2$ of the conserved motif L2, and $X_9$ of the conserved motif L3. It has been hypothesized that the presence of bulkier residues in the oxygen-tolerant hydrogenases may reduce the channel diameter at this point, thus limiting access of $O_2$ molecules, which are larger than $H_2$, to the active site. This hypothesis is now confirmed by independent studies on two different RHs ($H_2$ sensors) by Buhrke et al. (*J. Biol. Chem.* 2005, 280, 23791-23796) and Duché et al; (*FEBS J.* 2005, 272, 3899-3908)

On this basis, it has been suggested to modify naturally occurring hydrogenases in order to improve their resistance to dioxygen, by reducing the diameter of their $H_2$ channels. PCT application WO 2004/093524 thus proposes to modify [FeFe] hydrogenases by substituting the residues lining the $H_2$ channel by bulkier residues, such as tryptophan or phenylalanine.

SUMMARY OF THE INVENTION

The inventors have explored the effect on dioxygen tolerance of mutations at the positions occupied by Val74 and Leu122 (corresponding respectively to residue $X_2$ of the conserved motif L2, and residue $X_9$ of the conserved motif L3), in the [NiFe]-hydrogenase from *Desulfovibrio fructosovorans*.

On the basis of the prior art reports concerning the oxygen tolerant $H_2$-sensors, they first attempted to substitute valine with isoleucine at position 74 and leucine with phenylalanine at position 122. However, they observed that although the catalytic properties of the enzyme in anoxia were preserved, these substitutions did not improve dioxygen tolerance. In contrast, they found that, surprisingly, the replacement of Val74 and Leu122 with methionines provided an improved ability to sustain activity in the presence of $O_2$ and a far quicker recovery of a stable activity under reducing conditions when compared to the native hydrogenase.

The present invention provides means for improving dioxygen tolerance of [NiFe]-hydrogenases. The invention also provides modified [NiFe]-hydrogenases having a better oxygen tolerance than their native counterparts, while keeping a comparable catalytic activity.

An object of the present invention is a process for obtaining a mutant polynucleotide encoding a modified large subunit of a [NiFe]-hydrogenase, wherein said process comprises:

providing an initial polynucleotide comprising a sequence encoding a large subunit of a [NiFe]-hydrogenase, said large subunit comprising the following peptide motifs:

L1: RGXE, wherein X=L, I, F, V or M

L2: [R/K]$X_1$C[GIR]$X_2$C, wherein $X_1$ is any amino acid residue, $X_2$=L, V, I or M; L1 and L2 being separated by 16 any amino acid residues;

L3: $X_1X_2X_3X_4X_5X_6X_7X_8X_9X_{10}X_{11}X_{12}$[D/S/E], wherein $X_1$=D, S, N or E, $X_2$=H, D, S, N or L, $X_5$=H, S, A, Q or W, $X_6$=F, T, Y or (3, $X_9$=L, F, M or Y, the other $X_n$ being any amino acid residue;

L4: D[P/I/S]C$X_1X_2$C$X_3X_4$[H/R], wherein $X_2$=A, S, V, G or T, $X_3$ and $X_4$ are any amino acid residue and optionally comprising a motif L0: R[I/V/A]EG[H/D/A]

modifying said initial polynucleotide in order to substitute at least one of the residues $X_2$ of motif L2 and/or $X_4$ of motif L3 and/or $X_9$ of motif L3 of said large subunit by a methionine.

According to a preferred embodiment of the invention said process comprises modifying said initial polynucleotide in order to substitute the residue $X_4$ of motif L3 of said large subunit by a methionine.

According to another preferred embodiment of the invention said process comprises modifying said initial polynucleotide in order to substitute at least one of the residues $X_2$ of motif L2 and $X_9$ of motif L3 of said large subunit by a methionine.

According to another preferred embodiment, said initial polynucleotide is an operon further comprising the Sequence(s) encoding the other subunit(s) of said [NiFe]-hydrogenase.

The mutant polynucleotides obtainable by the above-described process are also part of the invention, as well as nucleic acid vectors containing said polynucleotides, and host cells genetically transformed by said vectors. Preferably, said vectors are expression vectors wherein the polynucleotide to be expressed is placed under transcriptional control of an appropriate promoter. The choice of suitable vectors and promoters depends on the host cell in which the polynucleotide will be transformed.

The invention also encompasses the modified large subunits of [NiFe]-hydrogenases encoded by the mutant polynucleotides of the invention, as well as the [NiFe]-hydrogenases containing said modified large subunits. Preferably, said [NiFe]-hydrogenases are encoded by the mutant operons of the invention.

Said modified [NiFe]-hydrogenases have an equivalent catalytic activity and an improved dioxygen tolerance when compared with the wild-type [NiFe]-hydrogenase from which they are derived. The modified [NiFe]-hydrogenases of the invention can be used in $H_2$ production. They are also useful in the development of bio-fuel cells, which can benefit from the availability of oxygen-tolerant catalysts, in order to yield more robust active surfaces, and eventually to get rid of membrane separation between hydrogen-oxidizing and dioxygen reducing electrodes (VINCENT et al., J Am Chem Soc, 127, 18179-89, 2005). Oxygen-tolerant [NiFe]-hydrogenases of the invention can also be employed in designing biosensors, to detect $H_2$ presence in air.

The mutant polynucleotides of the invention can be obtained by mutagenesis techniques, including in particular directed mutagenesis, which are well known in themselves. The modified large subunits, and the [NiFe]-hydrogenases of the invention can be obtained by expressing the polynucleotides of the invention in suitable host cells.

In the present case, suitable host cells for hydrogen photo-production include in particular cyanobacteria such as the cyanobacterium *Synechocystis* PCC6803 and by extension any cyanobacterium possessing a NiFe hydrogenase, the subunits of which are susceptible to be modified in the way described by the invention, by site-directed mutagenesis. Suitable host cells for producing hydrogenases which can be used as catalyst for fuel cells, electrolyzers or sensors are any bacterium in which a NiFe hydrogenase is present, is accessible to site directed mutagenesis and can be extracted and purified, in particular *Desulfovibrio fructosovorans* (see example 1).

Site directed mutagenesis and expression systems suitable for use in the above mentioned host cells are available in the art. For instance, shuttle vectors for *Desulfovibrio* (Rousset et al., Plasmid (1998), 39: 114-122. In the case of cyanobacteria, available systems are described in the following reviews: (i) Thiel T, Genetic analysis of cyanobacteria, in *The molecular biology of cyanobacteria*, D A Bryant (ed), Kluwer Academic Publishers, The Netherlands, 1994, pp 581-611; (ii) Elhai J. Genetic techniques appropriate for the biotechnological exploitation of cyanobacteria, Journal of Applied Phycology 6, 177-186, 1994; (iii) Porter R D Transformation in cyanobacteria, CRC Critical reviews in microbiology, 13(2), 111-132, 1986.

BRIEF DESCRIPTION OF THE DRAWINGS

The present invention is further illustrated by the additional description which follows, which refers to examples illustrating the preparation and properties of modified [NiFe]-hydrogenases of the invention. It should be understood however that these examples are given only by way of illustration of the invention and do not constitute in any way a limitation thereof.

FIGURE LEGENDS

Figure 1:
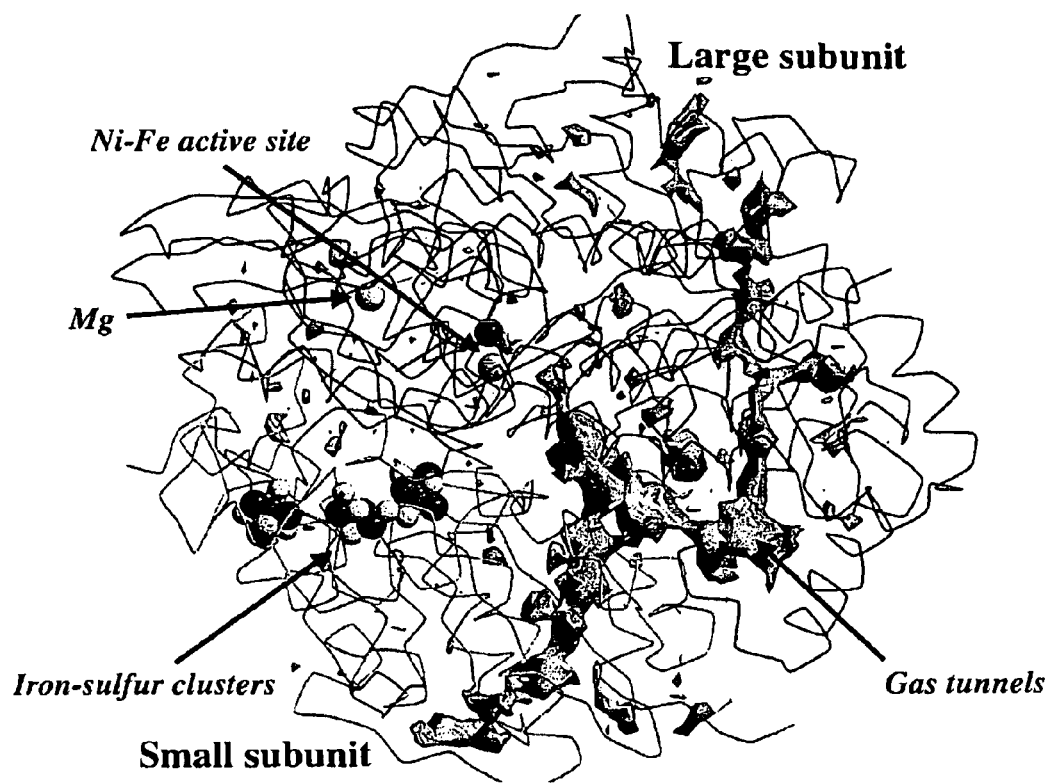

FIG. 1. Crystallographic structure of the [NiFe] hydrogenase from *D. fructosovorans* at 1.8 Å resolution (PDB: 1YQW). Location of the Ni—Fe active site and of the Fe—S clusters is indicated by the corresponding arrows. The gas channel is represented in grey, with a radius of 0.8 Å.

Figure 2:
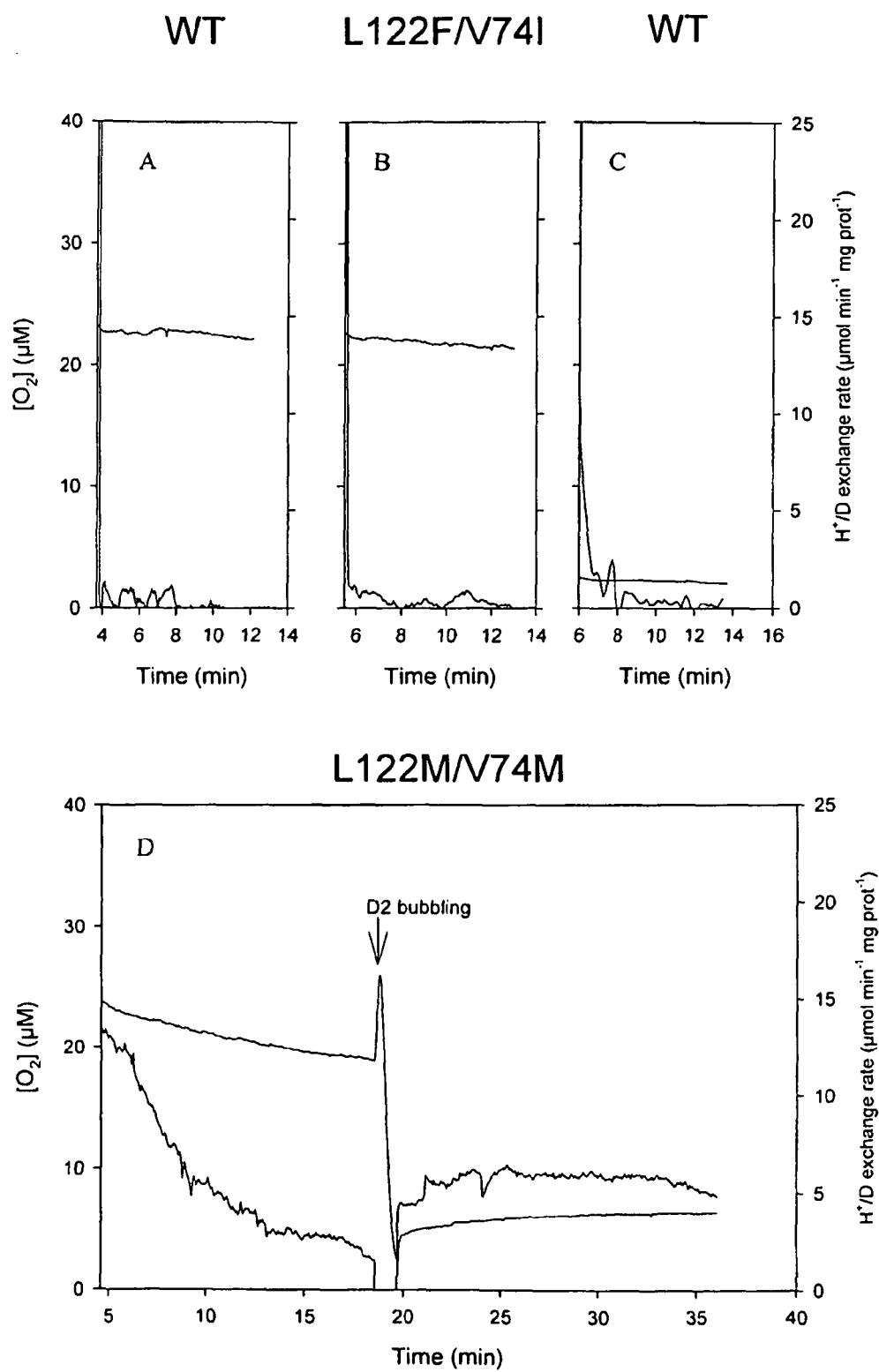

FIG. 2. Exchange activity assayed by MS. $D_2$ was bubbled into the medium in the vessel until $O_2$ was chased and decreased to the desired concentration, the vessel was then closed and an aliquot of activated hydrogenase was injected (at initial time in each graph) as explained in Example 2. In graph D, a second $D_2$ bubbling was performed at time=18 min. Dotted line: oxygen concentration, Black line: hydrogenase mediated isotope exchange rates (calculated at each point from $H_2$ and HD production rates obtained by numerically deriving gas concentration curves with respect to time using a 30 s time span for calculation).

Figure 3:
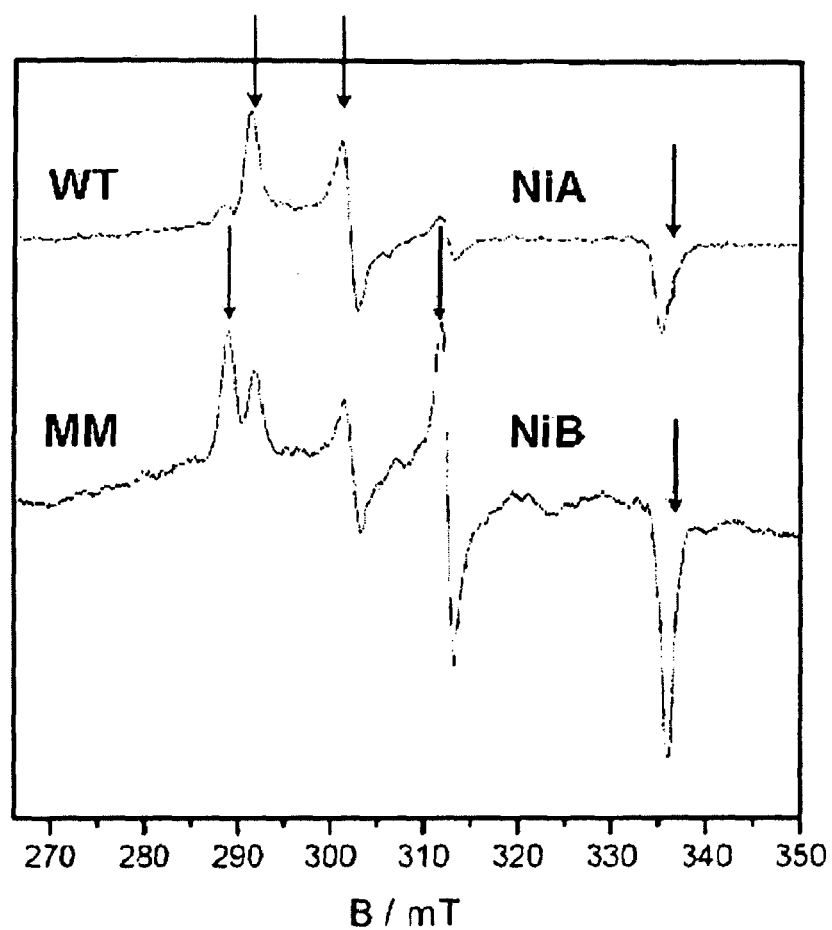

FIG. 3. EPR spectra of native hydrogenase and L122M-V74M-mutant in the oxidized state. The gx, gy and gz components of the Ni species Ni-A are indicated by the three arrows at upper position on the figure and those of the Ni species Ni—B are indicated by the three arrows at lower position. Experimental conditions: temperature, 100K; microwave power, 10 mW; modulation amplitude, 1 mT at 100 kHz.

Figure 4:
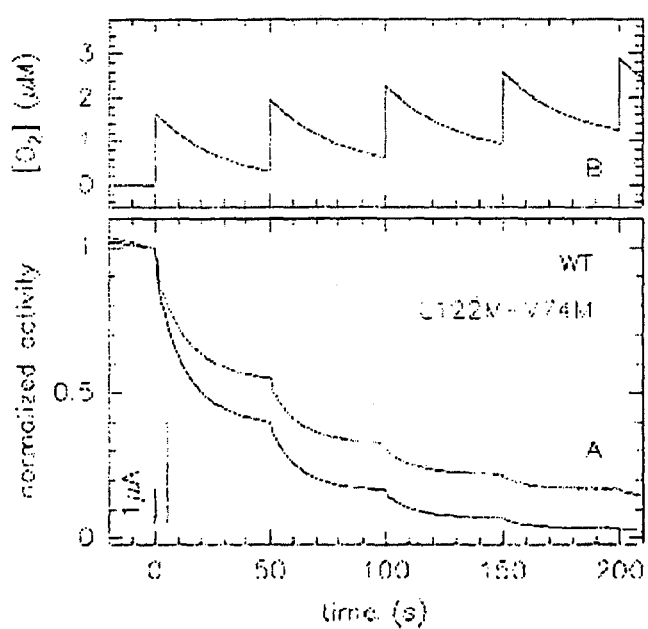

FIG. 4. Aerobic inactivation of WT and L122M-V74M *D. fructosovorans* [NiFe] hydrogenase. Activity (panel A) and oxygen concentration (panel B) against time, in protein film voltammetry experiments: The activity was measured as a current, and normalized by its value before aerobic inactivation began. Aliquots of air-saturated solution (five times 20 then three times 200 µL) were injected in electrochemical cell containing initially 3 mL of buffer. The current scales are indicated as bars on the bottom left corner. Electrode potential: 200 mV vs. SHE. T=40° C. pH 7. Electrode rotation rate omega=2 krpm.

Figure 5:
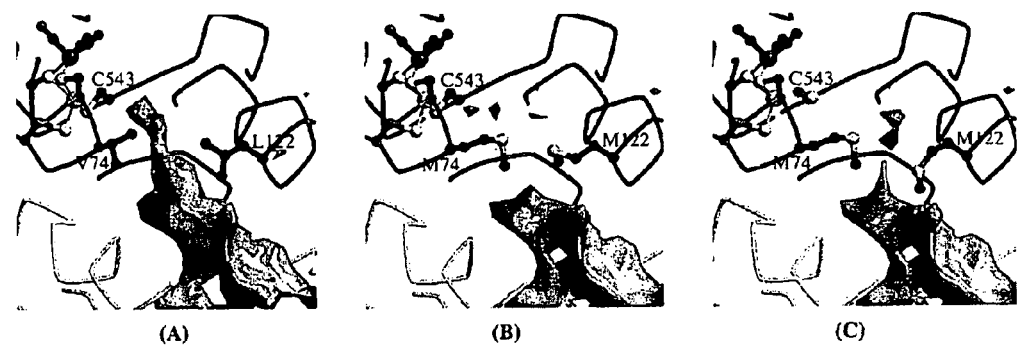

FIG. 5. Effect of mutations on gas channel gate in *D. fructosovorans* [NiFe]-hydrogenase. (A) Zoom of the region close to the native enzyme active site; (B) Same zoom for the V74M/L122M double mutant; (C) idem with alternative conformations for M122 and C543.

Figure 6:
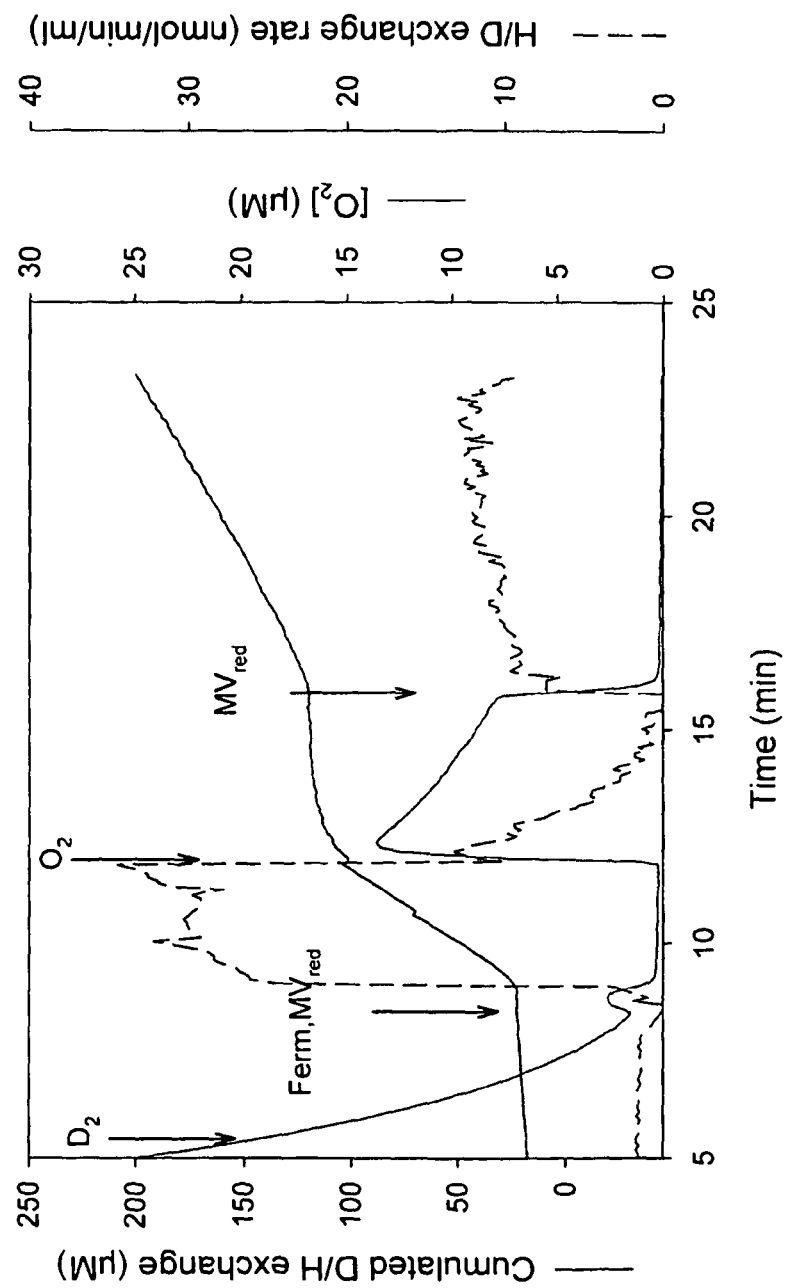

FIG. 6 represents the $H^+/D_2$ exchange activity assayed by MS and determined in *Synechocystis* cell-free extracts harboring the ΔhoxH strain of *Synechocystis* complemented with a wild-type copy of the hydrogenase gene. Dotted line: oxygen concentration. Solid line: hydrogenase mediated isotope exchange rates.

Figure 7:
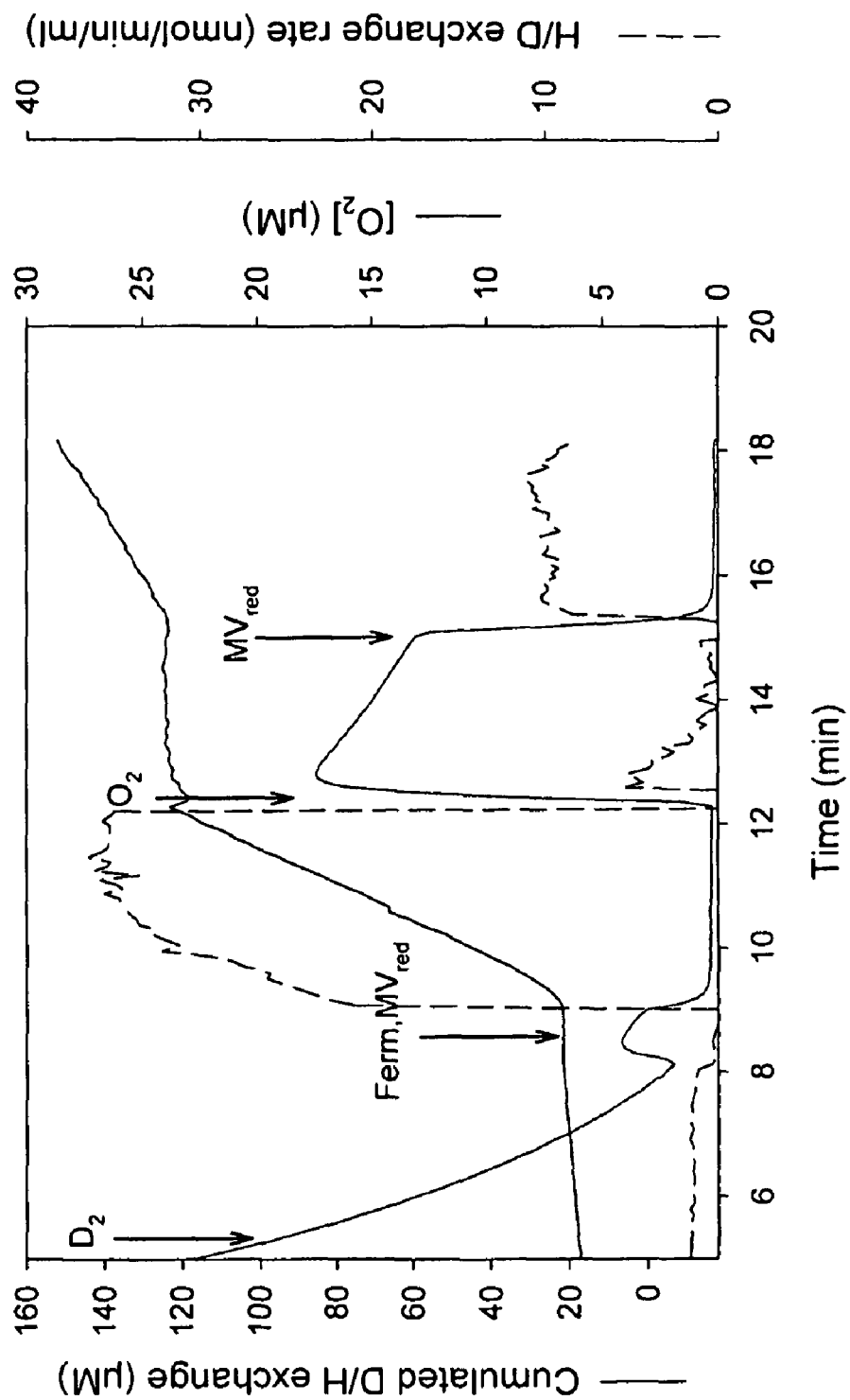

FIG. 7 represents the $H^+/D_2$ exchange activity assayed by MS and determined in *Synechocystis* cell-free extracts harboring the wild-type enzyme. Dotted line: oxygen concentration, Solid line: hydrogenase mediated isotope exchange rates.

Figure 8:
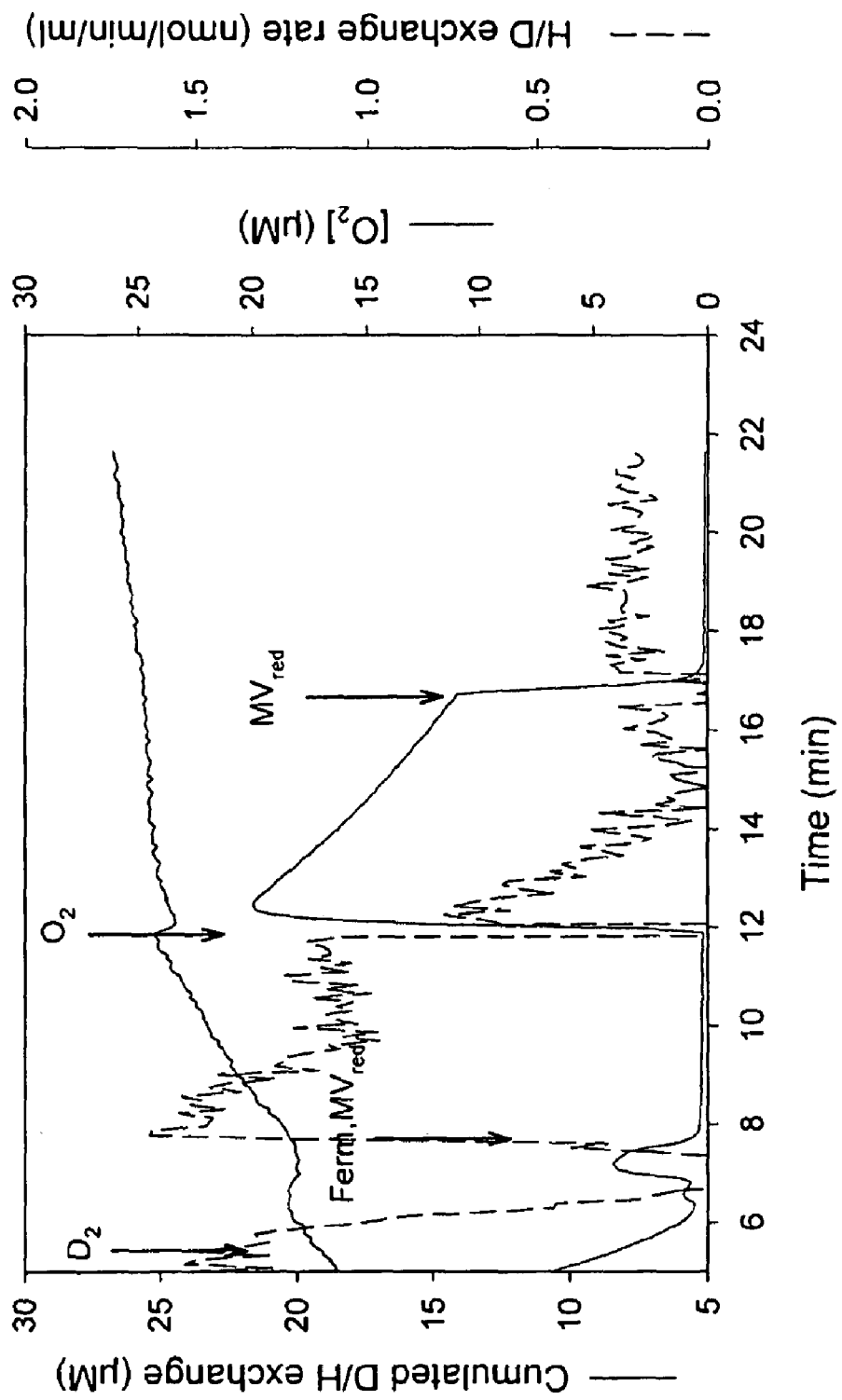

FIG. 8 represents the $H^+/D_2$ exchange activity assayed by MS and determined in *Synechocystis* cell-free extracts harboring the I64M-L112M HoxH mutant. Dotted line: oxygen concentration, Solid line: hydrogenase mediated isotope exchange rates.

Figure 9:
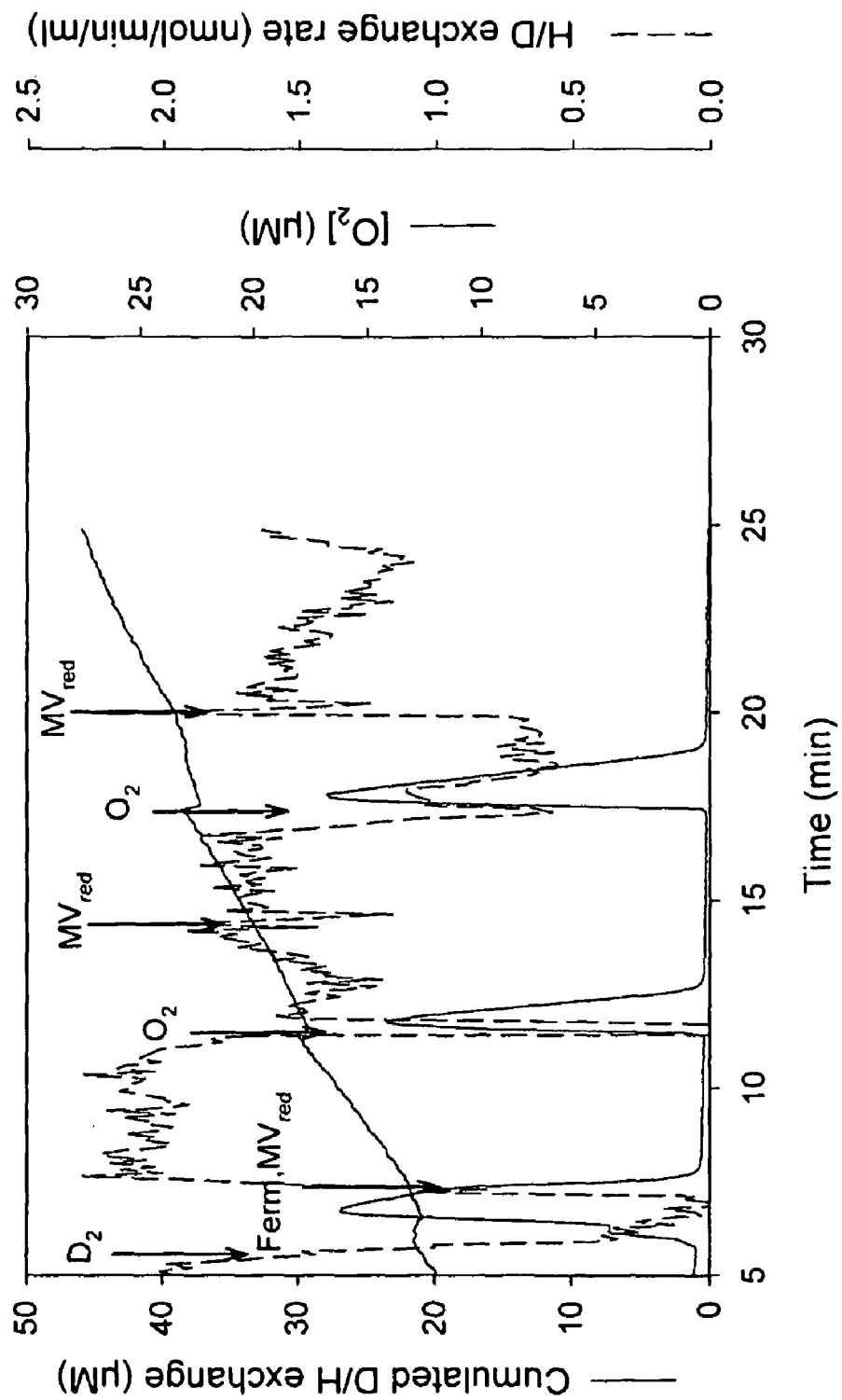

FIG. 9 represents the $H^+/D_2$ exchange activity assayed by MS and determined in *Synechocystis* cell-free extracts harboring the I64M-L107M HoxH mutant. Dotted line: oxygen concentration, Solid line: hydrogenase mediated isotope exchange rates.

Figure 10:
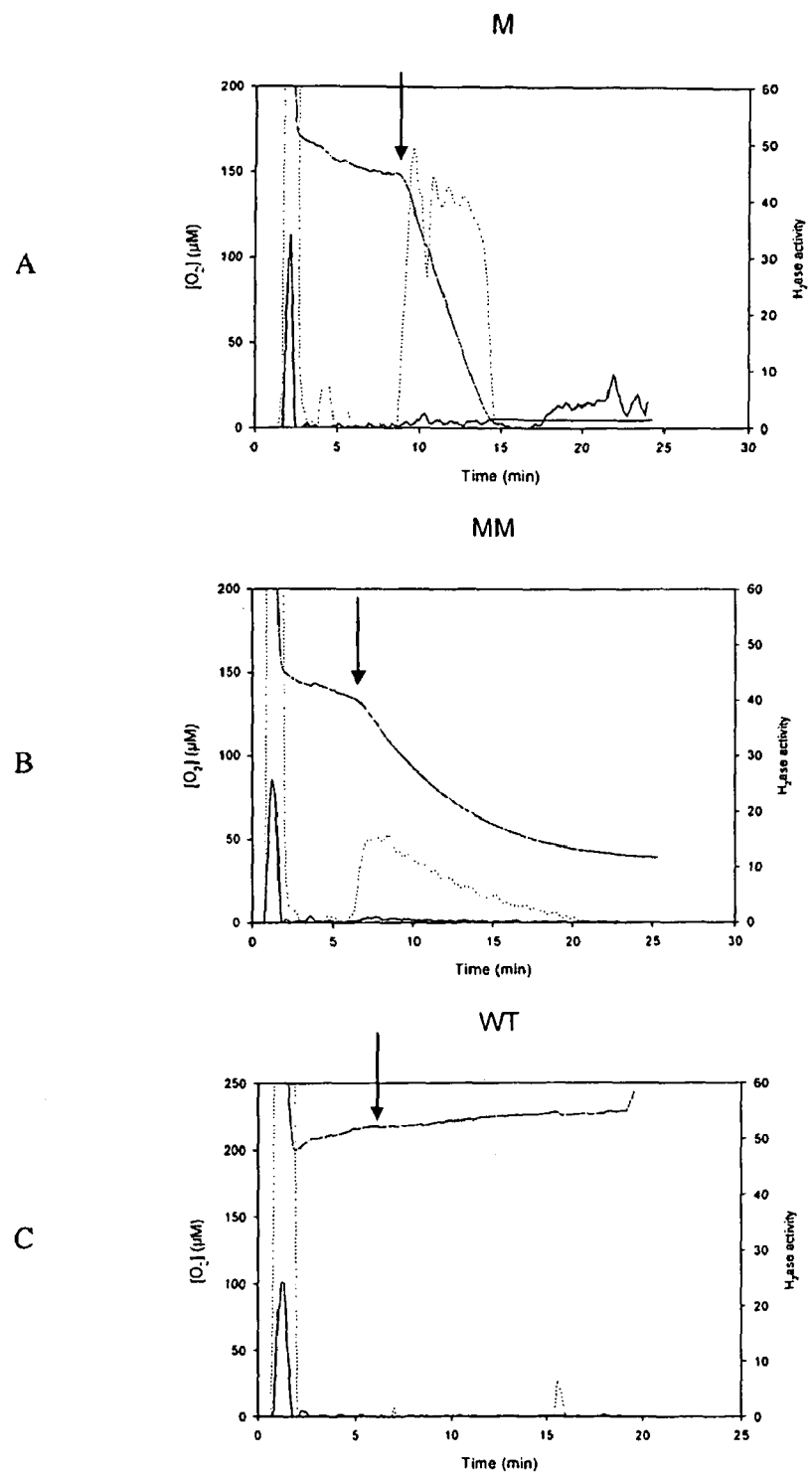

FIG. 10. Comparison of the inactivation at air oxygen concentration of V74M (denoted M), L122M-V74M (denoted MM) and wild-type (denoted WT) enzymes. The arrow indicates the injection of activated enzyme. The dashed lines represent the D2-consumption activity and the solid lines represent the $H^+/D_2$ exchange activity. The variation of the oxygen concentration in the medium is indicated by the arrowed line.

DETAILED DESCRIPTION OF THE INVENTION

Example 1

Construction and Expression of Mutant [NiFe] Hydrogenases

The effect on dioxygen tolerance of mutations of the hydrophobic residues $X_2$ of motif L2 and $X_9$ of motif L3 were studied in the large subunit hynB of the [NiFe]-hydrogenase from *Desulfovibrio fructosovorans* (from the [NiFe] hydrogenase operon GenBank M35333), where these residues are respectively Val74 and Leu122. The mutants V74M, L122F-V74I and L122M-V74M were constructed.

*D. fructosovorans* was used as a model because a genetic system allowing production of large amounts of recombinant hydrogenase has been developed in this organism (ROUSSET et al., Proc. Natl. Acad. Sci. USA, 95, 11625-30, 1998; DEMENTIN et al., J Biol Chem, 279, 10508-13, 2004).

Bacterial Strains, Plasmids and Growth Conditions

*Escherichia coli* strain DH5α, F−, endA1, hsdR17 ($r_K^-$ $m_K^+$), supE44, thi$^{-1}$, λ$^-$, recA1, gyrA96, relA1, Δ(argF$^-$ lacZYA) U169, φ80dlacZΔM15 was used as a host in the cloning of recombinant plasmids. The bacterium was routinely grown at 37° C. in LB medium. Ampicillin at 100 µg/ml or gentamycin at 20 µg/ml was added when cells harbored pUC18 or pBGF4 derivatives, respectively. The pBGF4 plasmid, which is a shuttle vector of the pBM family, reporting the gentamycin resistance gene (ROUSSET et al., Plasmid, 39, 114-22, 1998), was used to carry the [NiFe] hydrogenase operon from *D. fructosovorans* as described previously (ROUSSET et al., Proc. Natl. Acad. Sci. USA, 95, 11625-30, 1998).

*D. fructosovorans* strain MR400 [hyn::npt ΔhynABC] carrying a deletion in the [NiFe] hydrogenase operon (ROUSSET et al., Mol. Microbiol., 5, 1735-40, 1991) was grown anaerobically at 37° C. in SOS medium (ROUSSET et al. Plasmid, 39, 114-22, 1998). Large culture volumes were performed as described previously (ROUSSET et al., Proc. Natl. Acad. Sci. USA, 95, 11625-30, 1998). Kanamycine at 50 µg/ml was present routinely, and 50 gentamycin/ml were added only when cells harbored the plasmid pBGF4.

Site-Directed Mutazenesis.

The AatII-PstI fragment from pBGF4 was subcloned in pUC18 to generate the template that was used in mutagenesis experiments. The QuikChange™ XL site-directed mutagenesis kit (Stratagene, Amsterdam, The Netherlands) was used to generate point mutations in the large subunit hynB.

The substitution of valine 74 in methionine was performed by replacing guanine 1533 (According to the GenBank M35333 sequence numbering) from the GTG codon encoding valine by adenine to give the ATG codon encoding methionine. The substitution of valine 117 in methionine was performed by replacing guanine 1662 and cytosine 1664 (According to the M35333 sequence numbering) from the GTC codon encoding valine by adenine and guanine, respectively to give the ATG codon encoding methionine. The substitution of leucine 122 in methionine was performed by replacing cytosine 1677 (According to the M35333 sequence numbering) from the CTG codon encoding leucine by adenine to give the ATG codon encoding methionine.

After mutagenesis, the AatII-PsiI fragment was fully sequenced and inserted in the AatII-PstI digested pBGF4. The recombinant plasmid was introduced into *D. fructosovorans* strain MR400 by electroporation (ROUSSET et al., Plasmid, 39, 114-22, 1998).

Protein Purification.

The Strep tag II sequence (IBA Gmbh, Göttingen, Germany) was introduced in the hydrogenase gene: The tag S W S H P Q F E K plus a five amino acids linker G A S G A A was introduced on the N-terminal extremity of the large subunit. The enzyme was purified by affinity on a Strep-Tactin® column (IBA Gmbh) in a 100 mM Tris/HCl pH8, 0.5M Nacl Buffer. The elution was carried out as described by the manufacturer.

An additional purification step using a HiLoad™ 26/60 Superdex™ 200 prep grade column (Amersham Biosciences, Uppsala, Sweden) was performed. The purification yield of the recombinant M74/M122 hydrogenase was 2.25 mg of pure enzyme per liter of culture. The purification yield of the recombinant L122F-V74I was similar.

Example 2

Catalytic Activity of the WT, of the L122F-V74I, and of the L122M-V74M [NiFe]-Hydrogenases Hydrogenase activity was assessed in the presence of $O_2$ by monitoring the $H^+/D_2$ exchange activity, an intrinsic property of hydrogenase's active sites that does not involve electron transfer so that no catalytic reduction of dioxygen may occur.

$H^+$/Deuterium Exchange Reaction.

$H^+$/deuterium exchange in aqueous phase was monitored continuously by a membrane-inlet mass-spectrometric method (JOUANNEAU et al. J Bacteriol, 143, 628-36, 1980) at 30° C. in a 1.5 ml vessel containing 50 mM phosphate buffer, pH 7. Prior to measurements, hydrogenase was activated by incubation under an $H_2$ atmosphere in the presence of 100 µM MV. Anoxia of samples during activation was easily monitored by the blue color of reduced MV. The assay was then performed in the following way: $D_2$ was bubbled into the medium in the vessel until $O_2$ was chased and decreased to the desired concentration, the vessel was then closed and an aliquot of activated hydrogenase (20 µl of activated sample, representing 1 to 2.5 µg of enzyme) was injected (at initial time in the graphs composing FIG. 2). Hydrogenase activity was then calculated from velocity of isotopic exchange as exposed previously (COURNAC et al., J Bacteriol, 186, 1737-46, 2004).

The results are shown on FIG. 2.

As expected, the native enzyme inactivation was almost instantaneous at dioxygen concentrations around 10 µM and above (FIG. 2A). Some activity was detected soon after injection at lower $O_2$ concentrations (around 4 µM in FIG. 2B) which vanished within a few minutes. In addition, the native enzyme required prolonged incubation under reducing conditions to be reactivated. More surprisingly, the L122F-V74I mutant was inactivated in the same manner as the native enzyme (FIG. 2C).

The specific hydrogen-uptake activity of the L122M-V74M mutant was 320 U, which is comparable to that of the native hydrogenase (500 U). The inactivation of the L122M-V74M-mutant in the presence of about 20 µM dioxygen (FIG. 2D) was much slower than that of the native enzyme. Interestingly, $H^+/D_2$ exchange recovered to a large extent when $O_2$ concentration was set below 10 µM. About 50% of the initial activity was maintained under 6 mM $O_2$, a concentration at which the native enzyme is fully inhibited. These results show that the mutation confers two interesting features: i) the ability to sustain activity in the presence of $O_2$ and ii) the ability to recover a stable activity without the need for a prolonged reactivation under reducing conditions as required by the native hydrogenase.

Example 3

EPR Spectroscopy of the WT and of the L122M-V74M [NiFe]-Hydrogenases

The rapid reactivation of the L122M-V74M-mutant suggests that these mutations have a direct influence on the active site Ni—Fe ions. To investigate this influence, both the wild-type and the mutant hydrogenases were analyzed by EPR spectroscopy.

EPR spectra were recorded on a Brüker ESP 300E spectrometer fitted with an Oxford Instruments ESR 900 helium flow cryostat.

The results are shown on FIG. 3.

In the oxidized state of native hydrogenase, the NiFe center is present in a mixture of two EPR-active species, the unready Ni-A species (g=2.31, 2.24, 2.01) and the ready Ni-B species (g=2.32, 2.16, 2.01), the Ni-A species being the most abundant with Ni-A/Ni-B=80/20 (FIG. 3). In the case of the L122M-V74NI-mutant in the oxidised state, the ratio of the paramagnetic species is reversed with Ni-A/Ni-B=20/80 (FIG. 3).

It has been proposed that in the Ni-A species there is a peroxide ligand that bridges the Ni and Fe (OGATA et al., Structure (Camb), 13, 1635-42, 2005; VOLBEDA et al., 0.1 Biol Inorg Chem, 10, 239-49, 2005), which requires a prolonged reductive activation to be either removed or reduced (VOLBEDA et al. J Biol Inorg Chem, 10, 239-49, 2005; FERNANDEZ et al., Coordin. Chem. Rev., 249, 1596-608, 2005). In contrast, in the Ni-B species, the bridging ligand is thought to be a hydroxide ion that is easily removable under reducing conditions (VOLBEDA et al., J Biol Inorg Chem, 10, 239-49, 2005; FERNANDEZ et al., Coordin. Chem. Rev., 249, 1596-608, 2005).

In the native enzyme the Ni-A state is obtained only under aerobic oxidizing conditions whereas the Ni-B species can be formed upon anaerobic oxidation. The significant amount of Ni-B signal observed in the oxidized L122M-V74M-mutant is therefore fully consistent with its fast reactivation and suggests that the mutant's methionine side chains protect the enzyme by restricting dioxygen accessibility to the active site. The L122M-V74M-mutation has no effect on the reduced Ni-C active state of the enzyme or on the reduced iron-sulfur clusters, as measured by EPR spectroscopy, indicating that the mutated enzyme is fully matured and functional and that $H_2$ can reach the active site.

Example 4

Aerobic Inactivation of the WT and of the L122M-V74M [NiFe]-Hydrogenases

Protein film voltammetry was used to determine how the rate of aerobic inactivation is affected by the mutation. In this technique the enzyme is adsorbed onto an electrode so that direct electron transfer occurs, the activity is measured as a current and no soluble mediators need be used (LEGER et al., Biochemistry, 42, 8653-62, 2003).

Electrochemical measurements were performed as described previously (LEGER et al., J Am Chem Soc, 126, 12162-72, 2004). The pyrolytic graphite edge electrode onto which the enzymes adsorb was poised at +200 mV vs SHE, immerged in a solution at pH7, 40° C., continuously flushed with $H_2$, and the activity was measured as a current (FIG. 4A). Aliquots of aerated solution were repeatedly injected in the electrochemical cell and the resulting decrease in current against time reveals the aerobic inactivation of the enzyme: the faster the decrease in current, the greater the dioxygen sensitivity (LEGER et al., J Am Chem Soc, 126, 12162-72, 2004; DEMENTIN et al., J Biol Chem, 279, 10508-13, 2004; LAMLE et al., J Am Chem Soc, 126, 14899-909, 2004). The saw tooth-shaped plot of dioxygen concentration against time in FIG. 4B results from $O_2$ being flushed away by $H_2$. The dioxygen concentration profile in FIG. 4B was reconstructed from the amounts of aerated solution injected in the electrochemical cell, assuming an initial concentration of 250 μM $O_2$ in the air-saturated buffer. After each injection the $O_2$ concentration decreases exponentially with time and the time constant of the decay was determined by fitting the rate of the first inactivation as described in (LEGER et al., J Am Chem Soc, 126, 12162-72, 2004).

FIG. 4A compares the results of two inactivation experiments performed under exactly the same conditions. After exposure to sufficient amounts of $O_2$, both enzymes loose all activity. However, all things being equal, the MM-mutant inactivates significantly more slowly than the native enzyme. We determined that the mutation decreases the bimolecular rate constant for the reaction with dioxygen from 32 $s^{-1}mM^{-1}$ of $O_2$ (LEGER et al., J Am Chem Soc, 126, 12162-72, 2004) to 20 $s^{-1}mM^{-1}$, indicating that 1) the access of $O_2$ to the active site limits the rate of inactivation, and 2) that this process is slower in the mutant. Therefore the electrochemical experiments are also fully consistent with the notion that the mutant's methionine side chains block the active site cavity entrance to oxygen.

Example 5

Structure of the L122M-V74M [NiFe] Hydrogenase

The crystal structure of the L122M-V74M-mutant in the oxidised state was solved to determine the impact of the mutations on the shape of the gas tunnel, the reactivity of the methionines towards dioxygen and the possible modifications induced by the mutations in the active site cavity.

Crystals of the double methionine mutant of *D. fructosovorans* [NiFe]-hydrogenase were obtained and stored in liquid nitrogen as described for the S499A mutant (VOLBEDA et al., J Biol Inorg Chem, 10, 239-49, 2005). Diffraction data were collected at 100K on a square ADSC Q315R detector, using an X-ray wavelength of 1.0 Å at the ED23-1 beam line of the European Synchrotron Radiation Facility in Grenoble, France. In order to reduce radiation damage effects, three sets of images were collected from different parts of a cryo-cooled crystal. For each image a Δφ of 0.5° and an exposure time of 0.6 seconds were used. Diffraction spots were integrated, scaled and subjected to a zero-dose correction (DIEDERICHS et al., Acta Crystallogr D Biol Crystallogr, 59, 903-9, 2003) with XDS (KABSCH, International Tables for Crystallography, F, 2001). A final data reduction was performed with the CCP4 package (Anonymous, Acta Crystallogr D Biol Crystallogr, 50, 760-3, 1994). Intensity data statistics are given in Table 1 below.

TABLE 1

| | |
|---|---|
| Space group | $P2_1$ |
| Cell dimensions: β (°) | 91.6 |
| a, b, c (Å) | 64.6, 99.9, 183.0 |
| Molecules/asymmetric unit | 3 |
| Resolution (Å)* | 25-2.4 (2.5-2.4) |
| $R_{sym}$ (%) | 9.5 (24.0) |
| $<I>/<\sigma(I)>$* | 11.8 (4.4) |
| Number of observations* | 402274 (19482) |
| Unique reflections* | 86783 (8361) |
| Completeness (%)* | 95.3 (80.1) |
| Redundancy* | 4.6 (2.3) |

*numbers in parentheses refer to the highest resolution shell.

The crystal structure was refined with REFMAC (MURSHUDOV et al., Acta Crystallogr D Biol Crystallogr, 53, 240-55, 1997) with approximately the same strategy as described for the S499A mutant (VOLBEDA et al., J Biol Inorg Chem, 10, 239-49, 2005). The residues at the two mutation sites, Val74 and Leu122, were first changed into alanines and all water molecules were deleted from the starting model. After rigid body refinement of each subunit, methionines were modeled at positions 74 and 122 of the large subunits. Next, TLS bodies were used in order to model the overall anisotropic motions of each subunit (WINN et al., Acta Crystallogr D Biol Crystallogr, 57, 122-33, 2001) and typically, 10 cycles of TLS refinement and 10-15 cycles of refinement of atomic positions and isotropic temperate factors were alternated with manual model corrections using TURBO-FRODO (ROUSSEL & CAMBILLAU, 81, 1991), including water molecules where the electron density map indicated significant peaks at geometrically suitable positions. During refinement it became clear that the mutated residues were partially disordered. In the final model the side chain of Met74 has apparent 80-90% occupancy, depending on the enzyme molecule in the asymmetric unit, whereas Met122 has two conformations with about the same occupancy. Refinement statistics are shown in Table 2 below.

TABLE 2

| | |
|---|---|
| Resolution (Å) | 25-2.4 |
| Reflections in work set | 82430 |
| $R_{work}$ (%) | 14.7 |
| Reflections in test set | 4350 |
| $R_{free}$ (%) | 19.4 |
| Total number of atoms | 19338 |
| Water molecules | 718 |
| $\sigma_{bond}$ (Å) | 0.010 |
| $\sigma_{angle}$ (Å) | 1.20 |
| Average B-factors (Å$^2$)* | |
| Molecule 1 | 40.9 |
| Molecule 2 | 41.1 |
| Molecule 3 | 41.1 |

*excluding solvent molecules

Significant peaks in difference Fourier (Fobs-Fcalc) electron density maps indicated a mixture of at least two active site states among the three enzyme molecules present in the unit cell. For one of the three enzyme molecules, a peroxide ligand was modeled with 70% occupancy for the non-bridging oxygen atom, reflecting the fraction of unready Ni-A and/or Ni-SU species. The remaining 30% should then correspond to the hydroxide-containing Ni-B form. The other two molecules in the asymmetric unit contain a putative hydroxide bridge, in agreement with EPR results that indicated that most of the paramagnetic fraction of the enzyme is in the ready Ni-B state. These two molecules also display two conformations for the terminal Cys543 Ni-ligand, which are modelled with 70% and 30% occupancy, respectively (FIGS. 5 B and C). The changes induced by the mutations are highly localized, as no significant modifications were detected elsewhere in the structure. The mutant's Met74 and Met122 side chains did not react with dioxygen to form stable adducts, as indicated by their corresponding electron densities (not shown). As a consequence of the replacement of the native Val74 and Leu122 by the bulkier methionine residues, the gas tunnel at the interface with the active site cavity appears significantly narrower (FIGS. 5 B and C). However, the observed discrete disorder of the Met74 and Met122 side chains suggests that they may allow passage of gas molecules by fluctuating between different conformations. The nature of the side chain of the amino-acids located at the interface of the gas channel and the active site cavity is a crucial element in $O_2$ reactivity of *D. fructosovorans* [NiFe]-hydrogenase. Thus, steric hindrance does not seem to be the only determining parameter: the substitution of valine and leucine by isoleucine and phenylalanine, as inspired from oxygen-tolerant $H_2$-sensors, did not provide any oxygen tolerance. Further investigation will be needed to explain the difference in oxygen tolerance of the IF- and L122M-V74M-mutants. Maybe, the inherent higher flexibility of methionine side chains when compared with isoleucine or phenylalanine side chains is responsible for the observed phenotypes.

Example 6

Site Directed Mutagenesis of HoxH Subunit in Synechocystis PCC6803 and Catalytic Activity of the WT, of the HoxH AADA, of the I64M-L112Ni, and of the I64M-L107M Enzymes Strains and Growth Conditions

*Escherichia coli* strains XL1 Blue, HB101 and DH10β were used as a host in the cloning of the recombinant plasmids. The bacterium was routinely grown at 37° C. in LB medium. Ampicillin at 100 µg/ml or chloramphenicol at 50 µg/ml were added when cells harboured pUC18 or pUC19 derivatives.

Wild-type *Synechocystis* strain PCC 6803 and mutant strains were grown autotrophically in liquid modified Allen's medium (Allen, *J. Phycol.*, 4, 1-4, 1968) at 30° C. under continuous illumination, using one fluorescence tubular lamp, which provided an average light intensity of 30 mol of photons $m^{-2}s^{-1}$. Transformants were selected on Allen agar plates containing 25 µg chloramphenicol $ml^{-1}$ for the deletion mutant ΔhoxH or 25 µg spectinomycin $ml^{-1}$ for the mutants of the hoxH gene. Correct segregation of the transformants was checked by PCR.

Site-Directed Mutagenesis

The pUC19 plasmid, in which a sequence comprising the ORF of hoxH and 300 bp upstream and downstream (position 1673795 to 1671771 of the complete *Synechocystis* sequence (Kaneko et al. DNA Res., 3, 109-136, 1996) has been inserted, was subcloned in *Escherichia coli* cells and mutagenized. The QuickChange™ XL site-directed mutagenesis kit (Stratagene, Amsterdam, The Netherlands) was used to generate point mutations in the hoxH gene. The plasmid also contains a spectinomycin (await) resistance cassette inserted 50 bp after the ORF of hoxH. The final plasmid was completely sequenced. The residues I64, L107 and L112 in *Synechocystis* correspond to residues V74, L117 and L122 in *D. fructosovorans* respectively.

In order to insert mutagenized genes, a ΔhoxH strain of *Synechocystis* sp. PCC 6803 was first constructed by transforming the wild-type strain with pCC18 harbouring the following construct: the ORF of hoxH and 300 by upstream and downstream (position 1673795 to 1671771 of the complete sequence Kaneko et al. 1996) in which a chloramphenicol resistance cassette was inserted into Cla I restriction sites at position 19 and 1376 of hoxH. Indeed, starting from a deletion mutant is necessary due to the high number of chromosome copies in *Synechocystis*.

The resulting strain ΔhoxH was transformed with the modified pUC19 plasmid containing the mutants of hoxH. Strains harbouring the modified gene were then selected on spectinomycin as described above. I64M-L112M and I64M-L107M HoxH mutants were thus obtained.

$H^+$/Deuterium Exchange Reaction

Hydrogenase activity was assessed in the presence of $O_2$ by monitoring the $H^+/D_2$ exchange activity as described in Example 2. Results are shown on FIGS. 6-9.

FIGS. 6 and 7 are the controls: FIG. 6 represents the activity measured in the case of the ΔhoxH strain of *Synechocystis* sp. complemented with a wild-type (WT) copy of the hydrogenase gene (hoxH), and FIG. 7 represents the activity measured in the case of the WT enzyme.

FIG. 8 presents the activity measured in the I64M-L112M extract. When $O_2$ was injected, the activity first dropped and then increased to remain stable while $O_2$ was still present. The addition of reduced methyl viologen (MV) did not increase the activity.

In the case of the I64M-L107M mutant (FIG. 9), the hydrogenase activity appeared to be even more robust than for the I64M-L122M since several injections of $O_2$ were required to decrease the activity.

Example 7

Catalytic Activity of the WT, of the L122F-V74M, and of the V74M [NiFe]-Hydrogenases Hydrogenase activity of the wild-type (denoted WT), of the L122F-V74M (denoted MM), and of the V74M (denoted M) [NiFe]-hydrogenases was assessed in the presence of $O_2$ by monitoring the $H^+/D_2$ exchange activity.

The medium was bubbled with $D_2$ and left open, so that the $O_2$ concentration is closed to that in air. Results are shown on FIG. 10.

After injection, the M-mutant (V74M) was immediately active, It consumed $D_2$ and produced reduced methyl viologen (MV) that was oxidized by $O_2$. This reaction was followed by the consumption of $D_2$ (dashed line in graph A) and by the decrease of $O_2$ (top line in graph A) reduced by the methyl viologen (MV). When oxygen was present the electron flux was driven towards oxygen reduction, which prevented the exchange reaction to occur. When oxygen was eliminated, then the medium became fully reduced and the exchange reaction could start. This experiment demonstrates that the M-mutant is active in the presence of high oxygen concentration.

In the case of the MM-mutant (L122F-V74M), the enzyme was also active in the presence of 150 µM of $O_2$, but the kinetic was much slower. The enzyme became therefore inhibited by its longer exposure time to $O_2$.

As a control, the WT enzyme was readily inhibited by $O_2$.

CONCLUSION

In summary, the above results show for the first time that it is possible to improve dioxygen resistance of [NiFe]-hydrogenases. We have transformed an oxygen-sensitive hydrogenase into an oxygen-tolerant enzyme which is catalytically active in the presence of up to 20 µM of oxygen. Because there is no evidence that the introduced methionines react with dioxygen (FIG. 5), we conclude that they protect the enzyme most likely by preventing dioxygen to reach the active site. The L122M-V74M-mutant oxidised by dioxygen is in the same redox state as the native enzyme oxidised anaerobically (de LACEY et al., Coordin. Chem. Rev., 249, 1596-1608, 2005). This is clearly demonstrated by the main Ni-B EPR signal (FIG. 3) and the abundance of a hydroxyl bridging ligand at the active site. This protecting effect is responsible for the rapid reactivation (FIG. 2) and the slower inactivation rate (FIG. 4), the combination of which likely explains the ability of the modified enzyme to continuously function in presence of micromolar concentrations of $O_2$, which fully inactivate the WT.

The invention claimed is:

1. A process for obtaining a mutant polynucleotide encoding a modified large subunit of a wild-type $O_2$ sensitive [NiFe]-hydrogenase, for improving dioxygen tolerance of said [NiFe]-hydrogenase, wherein said process comprises:
  providing an initial polynucleotide comprising a sequence encoding a large subunit of a wild-type $O_2$ sensitive [NiFe]-hydrogenase having a hydrogenase activity, said large subunit comprising the following peptide motifs:
  L1: RGXE, wherein X=L, I, F, V or M
  L2: [R/K]$X_1$C[G/R]$X_2$C, wherein $X_1$ is any amino acid residue, $X_2$=L, V, I or M; L1 and L2 being separated by 16 any amino acid residues;
  L3: $X_1X_2X_3X_4X_5X_6X_7X_8X_9X_{10}X_{11}X_{12}$[D/S/E], wherein $X_1$=D, S, N or E, $X_2$=H, D, S, N or L, $X_5$=H, S, A, Q or W, $X_6$=F, T, Y or G, $X_9$=L, F, M or Y, the other $X_n$ being any amino acid residue;
  L4: D[P/I/S]C$X_1X_2$C$X_3X_4$[H/R], wherein $X_2$=A, S, V, G or T, $X_1$, $X_3$ and $X_4$ are any amino acid residue
  and optionally comprising a motif L0: R[I/V/A]EG[H/D/A];
  modifying said initial polynucleotide in order to substitute at least the residues $X_2$ of motif L2 of said large subunit by a methionine.

2. A process of claim 1, wherein said initial polynucleotide is further modified in order to substitute the residue $X_9$ of motif L3 of said large subunit by methionines.

3. A process of claim L wherein said initial polynucleotide an operon further comprising the sequence(s) encoding the other subunit(s) of said [NiFe]-hydrogenase.

4. A polynucleotide obtainable by the process of claim 1.

5. A polynucleotide obtainable by the process of claim 3.

6. A vector comprising a polynucleotide of claim 4.

7. An isolated host cell transformed by a vector of claim 6.

8. A modified large subunit of a [NiFe]-hydrogenase encoded by a polynucleotide of claim 4.

9. A modified [NiFe]-hydrogenase containing a modified large subunit of claim 8, wherein it has an equivalent hydrogenase activity and an improved dioxygen tolerance when compared with the wild-type $O_2$ sensitive [NiFe]-hydrogenase from which it is derived.

10. A [NiFe]-hydrogenase encoded by a polynucleotide obtained by a process comprising:
  providing an initial polynucleotide comprising a sequence encoding a large subunit of a wild-type $O_2$ sensitive [NiFe]-hydrogenase having a hydrogenase activity, said large subunit comprising the following peptide motifs:
  L1: RGXE, wherein X=I, F, V or M
  L2: [R/K]$X_1$C[G/R]$X_2$C, wherein $X_1$ is any amino acid residue, $X_2$=L, V, I or M; L1 and L2 being separated by 16 any amino acid residues;
  L3: $X_1X_2X_3X_4X_5X_6X_7X_8X_9X_{10}X_{11}X_{12}$[D/S/E], wherein $X_1$=D, S, N or E, $X_2$=H, D, S, N or L, $X_5$=H, S, A, Q or W, $X_6$=F, T, Y or G, $X_9$=L, F, M or Y, the other $X_n$ being any amino acid residue;
  L4: D[P/I/S]C$X_1X_2$C$X_3X_4$[H/R], wherein $X_2$=A, S, V, G or T, $X_1$, $X_3$ and $X_4$ are any amino acid residue
  and optionally comprising a motif L0: R[I/V/A]EG[H/D/A];
  modifying said initial polynucleotide in order to substitute the residues $X_2$ of motif L2 of said large subunit by a methionine, wherein said initial polynucleotide is an operon further comprising the sequence(s) encoding the other subunit(s) of said [NiFe]-hydrogenase;
  wherein said [NiFe]-hydrogenase has an equivalent hydrogenase activity and an improved dioxygen tolerance when compared with the $O_2$ sensitive [NiFe]-hydrogenase from which it is derived.

11. A process of claim 2, wherein said initial polynucleotide is an operon further comprising the sequence(s) encoding the other subunit(s) of said [NiFe]-hydrogenase.

12. A polynucleotide obtainable by the process of claim 2.

13. A vector comprising a polynucleotide of claim 5.

14. A process of claim 1, wherein said initial polynucleotide is further modified in order to substitute the residue $X_4$ of motif L3 of said large subunit by a methionine.

15. A process of claim 14, wherein said initial polynucleotide is an operon further comprising the sequence(s) encoding the other subunit(s) of said [NiFe]-hydrogenase.

16. A polynucleotide obtainable by the process of claim 14.

17. A vector comprising a polynucleotide of claim 16.

18. A process of claim 1, wherein said sequence encoding a large subunit of said wild-type [NiFe]-hydrogenase is from *Desulfovibrio fructosovorans*.

19. A process of claim 1, wherein said sequence encoding, a large subunit of said wild-type [NiFe]-hydrogenase is from a cyanobacterium.

20. A process of claim 19, wherein said sequence encoding a large subunit of said wild-type [NiFe]-hydrogenase is from Synechosystis.

21. A [NiFe]-hydrogenase of claim 10, wherein said initial polynucleotide is further modified in order to substitute the residue $X_9$ of motif L3 of said large subunit by a methionine.

22. A [NiFe]-hydrogenase of claim 10, wherein said initial polynucleotide is further modified in order to substitute the residue $X_4$ of motif L3 of said large subunit by a methionine.

23. A [NiFe]-hydrogenase of claim 10, wherein said sequence encoding a large subunit of said wild-type [NiFe]-hydrogenase is from *Desulfovibrio fructosovorans*.

24. A [NiFe]-hydrogenase of claim 10, wherein said sequence encoding a large subunit of said wild-type [NiFe]-hydrogenase is from a cyanobacterium.

25. A [NiFe]-hydrogenase of claim wherein said, sequence encoding a large subunit of said wild-type [NiFe]-hydrogenase is from *Synechosystis*.

26. A process of claim 1, wherein said nucleotide sequence is from a baeterium.

27. A [NiFe]-hydrogenase of claim 10, wherein nucleotide sequence from a bacterium.

* * * * *

UNITED STATES PATENT AND TRADEMARK OFFICE
CERTIFICATE OF CORRECTION

PATENT NO. : 8,377,671 B2
APPLICATION NO. : 12/671555
DATED : February 19, 2013
INVENTOR(S) : Cournac et al.

It is certified that error appears in the above-identified patent and that said Letters Patent is hereby corrected as shown below:

Column 1,
Line 33, a new paragraph should start with "Due to their high catalytic turnover".

Column 2,
Line 23, "Chema R" should read --Chenna R--;
Line 31, "[Fe]-hydrogenascs" should read --[Fe]-hydrogenases--;
Line 42, "*Bradyrhizobiurn*" should read --*Bradyrhizobium*--;
Line 44, "[NiFeSc]-hydrogenases" should read --[NiFeSe]-hydrogenases--.

Column 3,
Line 49, "[GIR]" should read --G/R--;
Line 54, "(3" should read --G--;
Line 57, "T, $X_3$" should read --T, $X_1$, $X_3$--.

Column 5,
Line 42, "voltammetry experiments:" should read --voltammetry experiments.--;
Line 44 and 45, "five times 20 then three times" should read --five times 20 µL then three times--;
Line 57, "ΔhoxH" should read --*ΔhoxH*--.

Column 6,
Line 27, "hynB" should read --*hynB*--;
Line 38, "end" should read --*end*-- and "hsd" should read --*hsd*--;
Line 39, "sup" should read --*sup*--, "thi" should read --*thi*--, "rec" should read --*rec*--, "gyr" should read --*gyr*--, "rel" should read --*rel*--, "arg" should read --*arg*--, and "lac" should read --*lac*--;
Line 40, "lac" should read --*lac*--;
Line 53, "ROUSSET et al." should read --ROUSSET et al.,--;
Line 57, "50 gentamycin/ml" should read --50 µg gentamycin/ml--;
Line 59, "Site-Directed Mutazenesis" should read --Site-Directed Mutagenesis--;
Line 64, "hynB" should read --*hynB*--.

Signed and Sealed this
Twenty-first Day of May, 2013

Teresa Stanek Rea
*Acting Director of the United States Patent and Trademark Office*

Column 7,
Line 11, "AatII-PsiI" should read --*Aat*II-*Pst*I--;
Line 12, "AatII-PstI" should read --*Aat*II-*Pst*I--;
Line 46, "JOUANNEAU et al." should read --JOUANNEAU et al.,--.

Column 8,
Line 11, "6 mM" should read --6 μM--;
Line 40, "L122M-V74NI-mutant" should read --L122M-V74M-mutant--;
Lines 45 and 46, "0.1 Biol" should read --J Biol--;
Line 48, "VOLBEDA et al." should read --VOLBEDA et al.,--.

Column 11,
Line 40, "I64M-L112Ni" should read --I64M-L112M--.
Line 54, "30 mol" should read --30 μmol--;
Line 57, "ΔhoxH" should read --*Δ*hoxH--;
Line 58 and 62, "hoxH" should read --*hoxH*--.

Column 12,
Lines 1, 10, 14, 18, and 29 "hoxH" should read --*hoxH*--;
Line 2, "(await)" should read --*(aadA)*--;
Lines 7, 17, and 27, "ΔhoxH" should read --*Δ*hoxH--;
Line 9, "pCC18" should read --pUC18--;
Line 10, "300 by" should read --300 bp--;
Line 55, "active," should read --active.--.

Column 19,
Line 4, "claim L" should read --claim 1--;
Lines 4 and 5, "polynucleotide an" should read --polynucleotide is an--;
Line 24, "X=I, F, V or M" should read --X = L, I, F, V or M--;
Line 40, "[NiFe]-hydrogenase;" should read --[NiFe]-hydrogenase,--;
Line 43, "O$_2$, sensitive" should read --O$_2$ sensitive--.

Column 20,
Lines 17 and 18, "encoding, a large subunit" should read --encoding a large subunit--;
Line 35, "claim wherein said, sequence" should read --claim 24, wherein said sequence--;
Line 39, "baeterium" should read --bacterium--;
Line 41, "sequence from" should read --sequence is from--.

UNITED STATES PATENT AND TRADEMARK OFFICE
CERTIFICATE OF CORRECTION

| | | |
|---|---|---|
| PATENT NO. | : 8,377,671 B2 | Page 1 of 1 |
| APPLICATION NO. | : 12/671555 | |
| DATED | : February 19, 2013 | |
| INVENTOR(S) | : Cournac et al. | |

It is certified that error appears in the above-identified patent and that said Letters Patent is hereby corrected as shown below:

Title page,
(75) Inventors: "Marseilles (FR)", both occurrences, should read --Marseille (FR)--;
"(73) Assignee: COMMISSARIAT A L'ENERGIE ATOMIQUE, Paris (FR)" should read
--(73), Assignees: COMMISSARIAT A L'ENERGIE ATOMIQUE, Paris (FR); CENTRE NATIONAL DE LA RECHERCHE SCIENTIFIQUE, Paris (FR)--.

Signed and Sealed this
Sixth Day of January, 2015

Michelle K. Lee
*Deputy Director of the United States Patent and Trademark Office*

SEQUENCE LISTING

```
<160> NUMBER OF SEQ ID NOS: 7

<210> SEQ ID NO 1
<211> LENGTH: 5
<212> TYPE: PRT
<213> ORGANISM: Artificial
<220> FEATURE:
<223> OTHER INFORMATION: Consensus sequence
<220> FEATURE:
<221> NAME/KEY: VARIANT
<222> LOCATION: (2)..(2)
<223> OTHER INFORMATION: /replace = Val or Ala
<220> FEATURE:
<221> NAME/KEY: VARIANT
<222> LOCATION: (5)..(5)
<223> OTHER INFORMATION: /replace = Asp or Ala

<400> SEQUENCE: 1

Arg Ile Glu Gly His
1               5

<210> SEQ ID NO 2
<211> LENGTH: 4
<212> TYPE: PRT
<213> ORGANISM: Artificial
<220> FEATURE:
<223> OTHER INFORMATION: Consensus sequence
<220> FEATURE:
<221> NAME/KEY: VARIANT
<222> LOCATION: (3)..(3)
<223> OTHER INFORMATION: /replace = Ile, Phe, Val or Met

<400> SEQUENCE: 2

Arg Gly Leu Glu
1

<210> SEQ ID NO 3
<211> LENGTH: 6
<212> TYPE: PRT
<213> ORGANISM: Artificial
<220> FEATURE:
<223> OTHER INFORMATION: Consensus sequence
<220> FEATURE:
<221> NAME/KEY: VARIANT
<222> LOCATION: (1)..(1)
<223> OTHER INFORMATION: /replace = Lys
<220> FEATURE:
<221> NAME/KEY: VARIANT
<222> LOCATION: (2)..(2)
<223> OTHER INFORMATION: /replace = Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: VARIANT
<222> LOCATION: (4)..(4)
<223> OTHER INFORMATION: /replace = Arg
<220> FEATURE:
```

```
<221> NAME/KEY: VARIANT
<222> LOCATION: (5)..(5)
<223> OTHER INFORMATION: /replace = Val, Ile or Met

<400> SEQUENCE: 3

Arg Ala Cys Gly Leu Cys
1               5

<210> SEQ ID NO 4
<211> LENGTH: 13
<212> TYPE: PRT
<213> ORGANISM: Artificial
<220> FEATURE:
<223> OTHER INFORMATION: Consensus sequence
<220> FEATURE:
<221> NAME/KEY: VARIANT
<222> LOCATION: (1)..(1)
<223> OTHER INFORMATION: /replace = Ser, Asn or Glu
<220> FEATURE:
<221> NAME/KEY: VARIANT
<222> LOCATION: (2)..(2)
<223> OTHER INFORMATION: /replace = Asp, Ser, Asn or Leu
<220> FEATURE:
<221> NAME/KEY: VARIANT
<222> LOCATION: (3)..(3)
<223> OTHER INFORMATION: /replace = Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: VARIANT
<222> LOCATION: (4)..(4)
<223> OTHER INFORMATION: /replace = Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: VARIANT
<222> LOCATION: (5)..(5)
<223> OTHER INFORMATION: /replace = Ser, Ala, Gln or Trp
<220> FEATURE:
<221> NAME/KEY: VARIANT
<222> LOCATION: (6)..(6)
<223> OTHER INFORMATION: /replace = Thr, Tyr or Gly
<220> FEATURE:
<221> NAME/KEY: VARIANT
<222> LOCATION: (7)..(7)
<223> OTHER INFORMATION: /replace = Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: VARIANT
<222> LOCATION: (8)..(8)
<223> OTHER INFORMATION: /replace = Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: VARIANT
<222> LOCATION: (9)..(9)
<223> OTHER INFORMATION: /replace = Phe, Met or Tyr
<220> FEATURE:
<221> NAME/KEY: VARIANT
<222> LOCATION: (10)..(10)
<223> OTHER INFORMATION: /replace = Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: VARIANT
<222> LOCATION: (11)..(11)
<223> OTHER INFORMATION: /replace = Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: VARIANT
<222> LOCATION: (12)..(12)
<223> OTHER INFORMATION: /replace = Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: VARIANT
<222> LOCATION: (13)..(13)
<223> OTHER INFORMATION: /replace = Ser or Glu

<400> SEQUENCE: 4

Asp His Ala Ala His Phe Ala Ala Leu Ala Ala Ala Asp
1               5                   10
```

```
<210> SEQ ID NO 5
<211> LENGTH: 9
<212> TYPE: PRT
<213> ORGANISM: Artificial
<220> FEATURE:
<223> OTHER INFORMATION: Consensus sequence
<220> FEATURE:
<221> NAME/KEY: VARIANT
<222> LOCATION: (2)..(2)
<223> OTHER INFORMATION: /replace = Ile or Ser
<220> FEATURE:
<221> NAME/KEY: VARIANT
<222> LOCATION: (4)..(4)
<223> OTHER INFORMATION: /replace = Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: VARIANT
<222> LOCATION: (5)..(5)
<223> OTHER INFORMATION: /replace = Ser, Val, Gly or Thr
<220> FEATURE:
<221> NAME/KEY: VARIANT
<222> LOCATION: (7)..(7)
<223> OTHER INFORMATION: /replace = Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: VARIANT
<222> LOCATION: (8)..(8)
<223> OTHER INFORMATION: /replace = Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: VARIANT
<222> LOCATION: (9)..(9)
<223> OTHER INFORMATION: /replace = Arg

<400> SEQUENCE: 5

Asp Pro Cys Ala Ala Cys Ala Ala His
1               5

<210> SEQ ID NO 6
<211> LENGTH: 13
<212> TYPE: PRT
<213> ORGANISM: Desulfovibrio fructosovorans

<400> SEQUENCE: 6

Asp His Leu Val His Phe Tyr His Leu His Ala Leu Asp
1               5                   10

<210> SEQ ID NO 7
<211> LENGTH: 13
<212> TYPE: PRT
<213> ORGANISM: Synechocystis PCC6803

<400> SEQUENCE: 7

Ser His Ala Leu Ser Phe Phe His Leu Ser Ser Pro Asp
1               5                   10
```